(12) United States Patent
Iannotti et al.

(10) Patent No.: US 10,307,174 B2
(45) Date of Patent: *Jun. 4, 2019

(54) APPARATUS AND METHOD FOR PROVIDING A REFERENCE INDICATION TO A PATIENT TISSUE

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 488 days.

This patent is subject to a terminal disclaimer.

(21) Appl. No.: 15/090,186

(22) Filed: Apr. 4, 2016

(65) Prior Publication Data

US 2016/0213385 A1 Jul. 28, 2016

Related U.S. Application Data

(63) Continuation of application No. 14/628,781, filed on Feb. 23, 2015, now Pat. No. 9,326,781, which is a
(Continued)

(51) Int. Cl.
*A61B 17/17* (2006.01)
*A61F 2/46* (2006.01)
(Continued)

(52) U.S. Cl.
CPC .......... *A61B 17/1739* (2013.01); *A61B 17/15* (2013.01); *A61B 17/1703* (2013.01);
(Continued)

(58) Field of Classification Search
CPC . A61B 17/17; A61B 17/1739; A61B 17/1703; A61B 17/15; A61F 2/46; A61F 2/4612
See application file for complete search history.

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

PCT International Search Report and Written Opinion dated Sep. 6, 2012, pp. 1-14.
(Continued)

*Primary Examiner* — Christopher Beccia
(74) *Attorney, Agent, or Firm* — Norton Rose Fulbright Canada LLP

(57) ABSTRACT

An apparatus for providing a reference indication to a patient tissue includes a primary locating block having a patient-specific primary mating surface contoured for mating contact with a portion of the patient tissue in a predetermined primary mating orientation custom-configured responsive to preoperative imaging of the patient tissue. At least one mounting feature is provided to the primary locating block. At least one secondary item is configured for selective engagement with the primary locating block. The secondary item is at least one of a noncustomized secondary item and a patient-specific secondary item. The secondary item provides a reference indication to at least a portion of the patient tissue. The mounting feature of the primary locating block is configured for engagement with at least one secondary item in a predetermined secondary mounting relationship. The secondary mounting relationship is custom-configured for the patient tissue responsive to preoperative imaging of the patient tissue.

20 Claims, 11 Drawing Sheets

Related U.S. Application Data continuation of application No. 13/472,662, filed on May 16, 2012, now Pat. No. 8,992,539.

(60) Provisional application No. 61/487,908, filed on May 19, 2011.

(51) Int. Cl.
*A61B 17/15* (2006.01)
*A61B 17/56* (2006.01)

(52) U.S. Cl.
CPC .............. *A61F 2/46* (2013.01); *A61F 2/4612* (2013.01); *A61B 17/1778* (2016.11); *A61B 2017/568* (2013.01); *A61F 2002/4635* (2013.01); *A61F 2002/4687* (2013.01)

(56) References Cited

U.S. PATENT DOCUMENTS

| | | | |
|---|---|---|---|
| 5,490,854 A | 2/1996 | Fisher et al. | |
| 5,607,431 A | 3/1997 | Dudasik et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 6,206,884 B1* | 3/2001 | Masini .................. | A61B 17/15 606/89 |
| 6,780,190 B2 | 8/2004 | Maroney | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 9,145,642 B2 | 9/2015 | Kurosu | |
| 9,326,781 B2* | 5/2016 | Iannotti .................. | A61B 17/15 |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0234461 A1 | 10/2005 | Burdulis et al. | |
| 2005/0245934 A1 | 11/2005 | Tuke et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0234685 A1 | 9/2008 | Gjerde | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1* | 11/2008 | Kunz ................... | A61B 17/175 606/87 |
| 2009/0018546 A1* | 1/2009 | Daley .................. | A61B 17/175 606/92 |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |

(56) References Cited

U.S. PATENT DOCUMENTS

| | | |
|---|---|---|
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 * | 3/2011 | Metzger ............... A61B 17/157 606/88 |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0190775 A1 | 8/2011 | Ure |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |

(56) References Cited

U.S. PATENT DOCUMENTS

| | | |
|---|---|---|
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 1925799 A | 10/2010 |
| CN | 1633265 A | 12/2010 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A2 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |

(56) References Cited

FOREIGN PATENT DOCUMENTS

| | | |
|---|---|---|
| HK | 1087324 A1 | 11/2011 |
| HK | 1104776 A1 | 11/2011 |
| JP | 2006510403 A | 3/2006 |
| JP | 2007514470 A | 6/2007 |
| JP | 2010540123 A | 12/2010 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2009001083 A | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011018647 A1 | 2/2011 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Taylor et al, "Computer-Integrated Surgery, Technology and Clinical Applications", The MIT Press, Cambridge, MA, London, UK, pp. 451-463.

Hofmann et al, "Natural-Knee II System", Intermedics Orthopedics, Austin, TX, 1995.

* cited by examiner

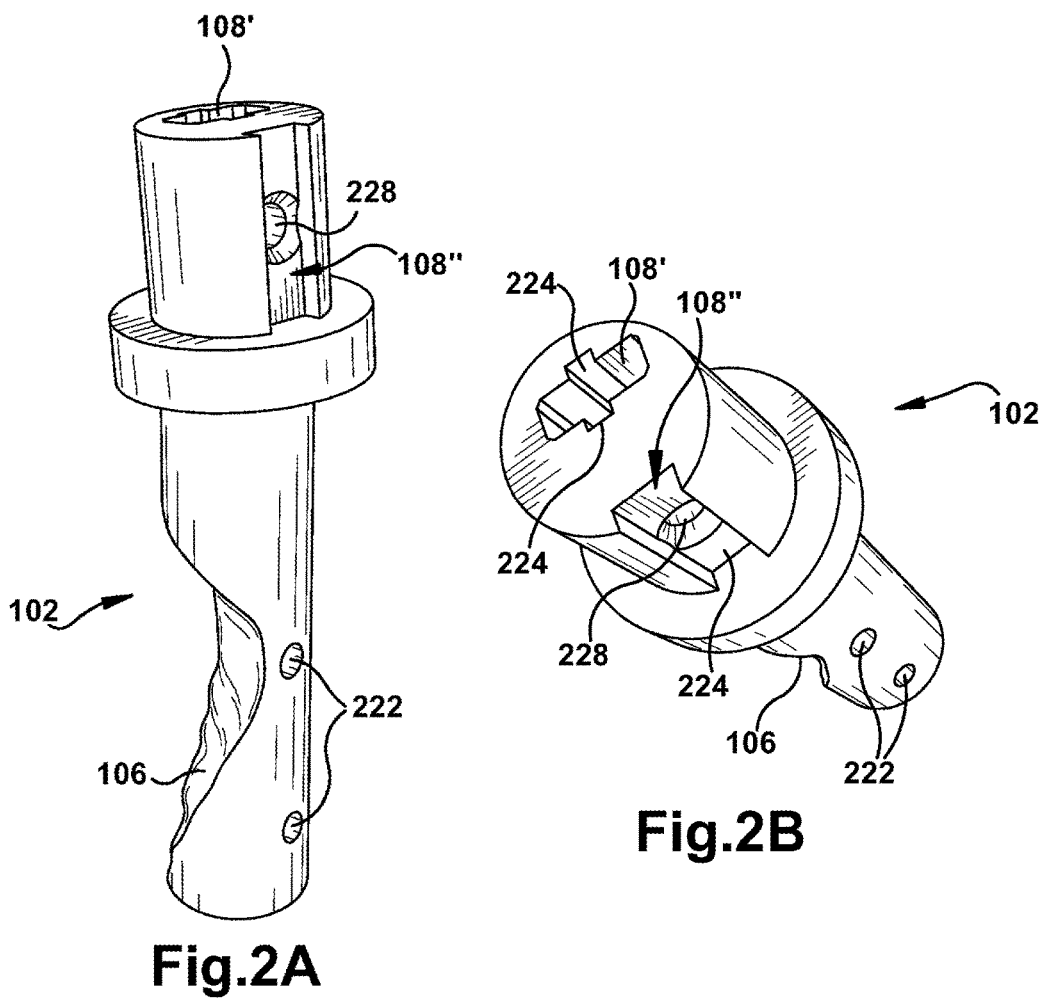

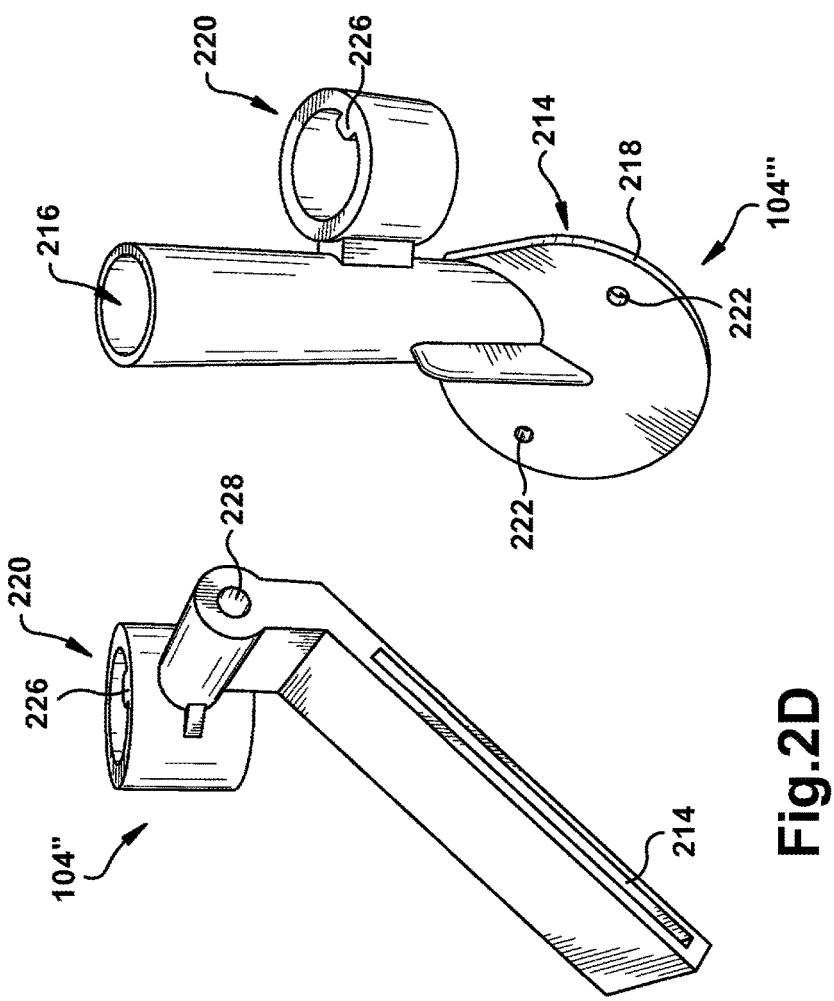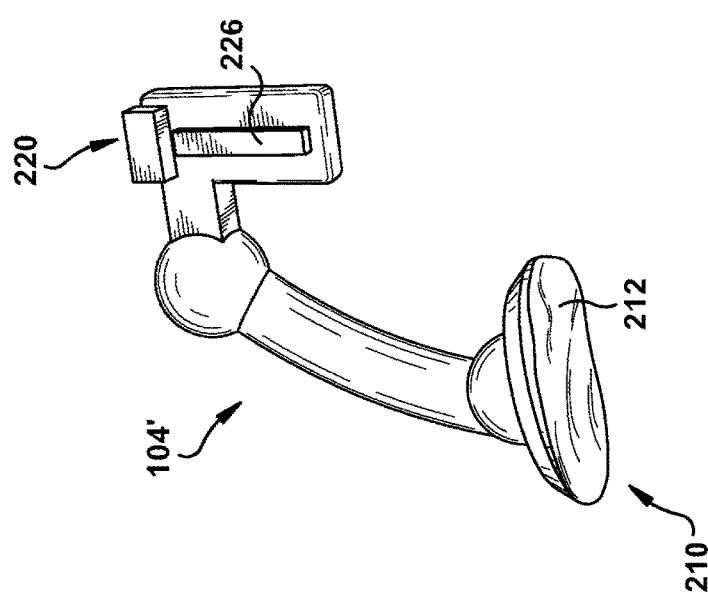

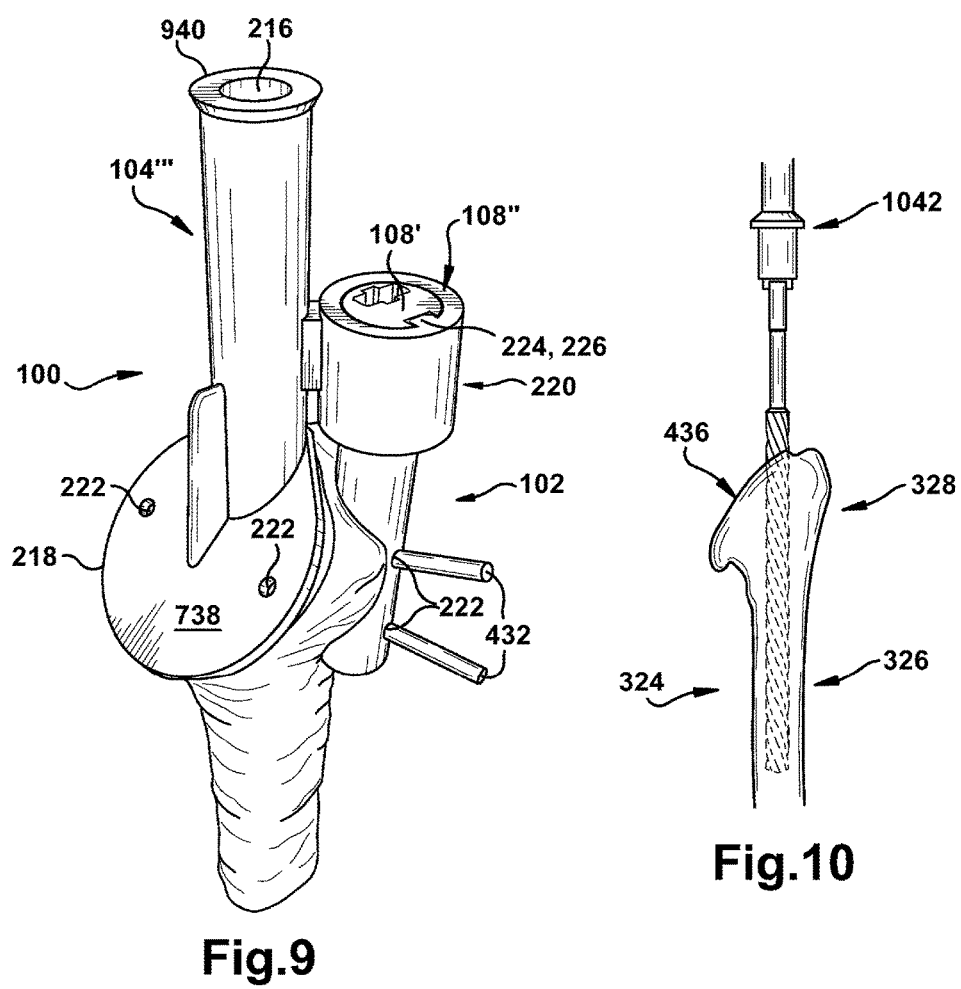

APPARATUS AND METHOD FOR PROVIDING A REFERENCE INDICATION TO A PATIENT TISSUE

RELATED APPLICATION

This is a continuation non-provisional application Ser. No. 14/628,781 filed on Feb. 23, 2015 which is a continuation non-provisional application Ser. No. 13/472,662 filed on May 16, 2012 which claims priority from U.S. Provisional Application No. 61/487,908, filed 19 May 2011, the subject matter of which is incorporated herein by reference in its entirety.

TECHNICAL FIELD

The present invention relates to an apparatus and method for providing a reference indication to a patient tissue and, more particularly, to a method and apparatus for guiding resection and modification of a patient tissue to receive a prosthetic implant component in a desired implant position.

BACKGROUND OF THE INVENTION

Minimally invasive surgery ("MIS") is quickly becoming standard for the implantation of prosthetic components into a patient. For example, the use of an MIS shoulder replacement technique involves a skin incision of approximately 7-9 cm and is performed without the previously required laying-open of the patient's entire shoulder area. MIS techniques for joint replacement may reduce trauma to the patient, with less pain, less blood loss, shorter convalescence, faster stabilization, and fewer post-operative restrictions on exercising of the joint. The use of MIS may also give the prosthetic joint a better fixation and function than traditional surgery, which in turn can contribute to an increased lifetime for the prosthetic joint. MIS also can be done with considerably shorter hospitalization time than traditional techniques, and may even be available for out-patient procedures, providing an economic benefit linked to positive patient outcome in many cases.

In a prosthetic shoulder joint replacement, whether accomplished via MIS or any other suitable surgical technique, the humeral head is removed and replaced with a prosthetic head which is fixed to the bone using a stem within the humeral metaphysis and/or diaphysis shaft. The humeral head articulates with the native glenoid (hemiarthroplasty) or with a prosthetic glenoid component. The humeral osteotomy is made at or near the anatomic neck of the humerus. This osteotomy defines a humeral head neck shaft angle and version of the final implant. In patients with deformity associated with arthritis, the anatomic neck is difficult to define, making it difficult for the surgeon to determine to precise location of this osteotomy. Standard generic stock cutting guides currently used for this procedure still require the surgeon to identify these anatomic landmarks to place the cutting guides.

One factor which may lead to success for a total shoulder replacement technique is the provision of a clear overall view of the wound during the operation in order to achieve precise surgery and the desired positioning for the prosthetic components. In the precise surgery associated with the implantation of a shoulder replacement prosthetic component, it is important for the head of the humerus to be removed with great precision. For this purpose an osteotomy template is generally used, whereby the level and orientation of the planned cutting plane is transferred to the patient's humerus to guide the surgeon. With the preoperative planning procedures that are currently under development, a computer model of the patient's humerus will often be produced, based on CT, radiographic, or other preoperatively obtained images. Based on this model, a desired cutting plane for the patient's humerus can be determined.

Osteotomy templates exist for use in conventional surgery, but there is currently a need for improved osteotomy templates. A resection guide for use in many hip, shoulder, or other types of prosthetic replacements, whether using MIS or another surgical style, would be useful than currently used guides by being considerably smaller, intended for insertion through different openings, employing different anatomical landmarks, allowing for a more accurate osteotomy, and easier to position in the planned position than the currently used resection guides.

Since traditional osteotomy templates are not adapted to the individual patient, they require the surgeon to remove pathologic bone to identify landmarks in order to place the template and make a cut or to use the anatomic landmarks to make an osteotomy without any template or cutting guide. The difficulty lies in the surgeon's ability to identify anatomic landmarks in the pathologic condition. This means that for patients with anatomical deviations, there is a reduction in precision with traditional multi-use osteotomy templates, thereby giving a final result that is not optimal. For patients with greater anatomical deviations, moreover, the majority of multi-use templates will be difficult to use on account of limitations in the possibilities for adjustment. Even for patients without great deviations, when using multi-use templates it will be necessary to carry out adjustments of the osteotomy template during the operation, resulting in an increased risk of error, increased operating time and thereby an increased risk of complications.

SUMMARY OF THE INVENTION

In an embodiment of the present disclosure, there is provided an apparatus for providing a reference indication to a patient humerus, the apparatus comprising: a primary locating block including a patient-specific primary mating surface contoured and configured for mating contact with at least a portion of a diaphysis of the humerus, the primary mating surface being custom-configured to mate with the humerus in a predetermined primary mating orientation responsive to preoperative imaging of the patient humerus, and at least one mounting feature; and at least one secondary item configured for selective engagement with the primary locating block and including a patient-specific secondary mating surface being contoured and configured for mating contact with at least a portion of the epiphysis of the humerus, the secondary item being custom-configured to mate with the humerus in a predetermined secondary mating orientation responsive to preoperative imaging of the humerus, the secondary mating orientation being non-coincident with the primary mating orientation, and the secondary item providing a first reference indication to the portion of the epiphysis of the humerus; wherein the mounting feature of the primary locating block is configured for engagement with the at least one secondary item in a predetermined secondary mounting relationship, the secondary mounting relationship being custom-configured for the patient humerus responsive to preoperative imaging of the patient humerus such that the primary locating block and the at least one secondary item are in the predetermined secondary mounting relationship when respectively and concurrently in said mating contact with at least the diaphysis and the epiphysis of the patient humerus.

In an embodiment of the present disclosure, there is provided a method of providing a reference indication to a patient humerus, the method comprising: obtaining a primary locating block including a patient-specific primary mating surface contoured and configured for mating contact with at least a portion of a diaphysis of the humerus, and at least one mounting feature; mating the primary mating surface with the patient humerus in a primary mating orientation predetermined at least partially responsive to preoperative imaging of the patient tissue; obtaining at least one secondary item including a patient-specific secondary mating surface being contoured and configured for mating contact with at least a portion of the epiphysis of the humerus; engaging the mounting feature of the primary locating block with the at least one secondary item in a predetermined secondary mounting relationship, the secondary mounting relationship being custom-configured for the patient humerus responsive to preoperative imaging of the patient humerus; and mating the secondary mating surface with the patient humerus in a secondary mating orientation predetermined at least partially responsive to preoperative imaging of the patient humerus, the secondary mating orientation being non-coincident with the first mating orientation; obtaining a first reference indication to at least a portion of the patient humerus with the secondary item when the primary mating surface and the secondary mating surface are respectively and concurrently in said mating with at least the diaphysis and the epiphysis of the patient humerus.

In an embodiment of the present invention, a system for facilitating at least one of resection, repositioning, drilling, trimming, and configuration verification of a patient tissue of a long bone is provided. A primary locating block includes a patient-specific primary mating surface contoured for mating contact with a nontarget portion of the long bone. The primary mating surface is custom-configured to mate with the nontarget portion of the patient tissue in a predetermined primary mating orientation responsive to preoperative imaging of the long bone. At least one mounting feature is provided to the primary locating block. At least one secondary item is configured for selective engagement with the primary locating block. The secondary item is at least one of a noncustomized stock secondary item and a patient-specific secondary item. The secondary item provides a reference indication to at least a portion of the long bone to facilitate at least one of resection, repositioning, drilling, trimming, and configuration verification of a target portion of a long bone. The mounting feature of the primary locating block is configured for engagement with at least one secondary item in a predetermined secondary mounting relationship. The secondary mounting relationship is custom-configured for the long bone responsive to preoperative imaging of the long bone.

BRIEF DESCRIPTION OF THE DRAWINGS

For a better understanding of the invention, reference may be made to the accompanying drawings, in which:

FIGS. 2A-2E are individual perspective views of various components of the embodiment of FIG. 1;

FIGS. 4-9 illustrate a sequence of operation of the embodiment of FIG. 1 in the use environment of FIG. 3;

FIG. 10 schematically depicts a surgical step in the sequence of operation of FIGS. 4-9.

DESCRIPTION OF EMBODIMENTS

Figure 1:
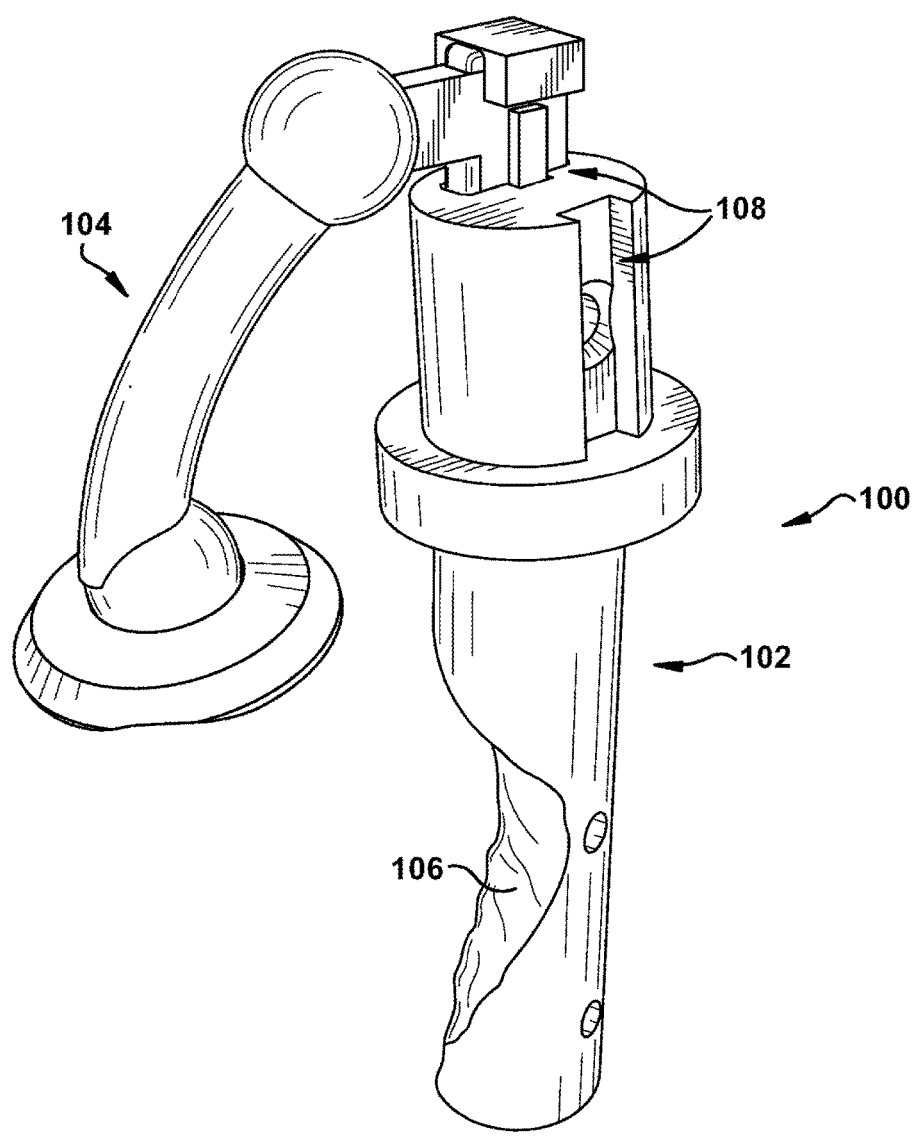
FIG. 1 is a perspective side view of a configuration of an embodiment of the present invention.

In accordance with the present invention, FIG. 1 depicts an example configuration of an apparatus 100 for providing a reference indication to a patient tissue (omitted from the view of FIG. 1) and which may be used for guiding resection and modification of a patient tissue to receive a prosthetic implant component in a desired implant position, or for any other desired purpose. The patient tissue is shown and described herein at least as a humeral long bone and the implant component is shown and described herein at least as a humeral prosthetic shoulder component of a known type having a stem inserted into a bored-out humeral intramedullary canal. However, the patient tissue and corresponding implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention. For example, the implant component could be an internal fixation device (e.g., a bone plate), a structure of a replacement/prosthetic joint, or any other suitable artificial device to replace or augment a missing or impaired part of the body. The implant component will be described herein as a prosthetic implant component.

The apparatus 100 includes a primary locating block 102 and at least one secondary item 104 configured for selective engagement with the primary locating block. The primary locating block 102 includes a patient-specific primary mating surface 106 which is contoured for mating contact with at least a portion of the patient tissue. The term "mating" is used herein to indicate a relationship in which the contours of two structures are at least partially matched or coordinated in at least two dimensions. For example, both the primary mating surface 106 and the patient tissue surface could have profiles that are concavely curved, convexly curved, planar/linear, or any combination of those or other profile shapes. The primary mating surface 106 may be custom-configured to mate with the patient tissue in a predetermined primary mating orientation responsive to preoperative imaging of the patient tissue. The primary locating block also may include at least one mounting feature 108 (two shown).

FIGS. 2A-2E are individual perspective views of various components of the apparatus 100 shown in FIG. 1, and include detail on the secondary mounting relationships between each secondary item 104 and the primary locating block 102. FIGS. 2A and 2B depict different aspects of the primary locating block 102. The primary mating surface 106 of the primary locating block 102 is shown in the view of FIG. 2A. While it is possible for the primary mating surface 106 to be substantially two-dimensional (e.g., an irregular line) for substantially linear contact with the patient tissue, it is contemplated that, for many applications of the present invention, the primary mating surface 106 will be three-dimensional for mating with a corresponding part or layer of the patient tissue, as shown in FIGS. 2A and 2B.

The secondary item 104' shown in FIGS. 1 and 2C includes a positioning indicator 210 which can help to verify the position of at least a portion of the apparatus 100 with respect to the patient tissue. In order to do so, the positioning indicator 210 has a patient-specific secondary mating surface 212 which may be custom-configured to mate with a portion of the patient tissue in a predetermined secondary mating orientation responsive to preoperative imaging of the patient tissue. The secondary mating orientation may be non-coincident with the primary mating orientation. That is, the portion of the patient tissue mated with the secondary mating surface 212 may be different from the portion of the patient tissue mated with the primary mating surface 106, though the two portions of the patient tissue may be adjacent or even contiguous, depending upon the configuration of the apparatus 100. The property of "non-coincidence" is independent of the timing of the mating of the surface(s) with the patient tissue, as the primary and secondary mating surfaces 106 and 212 could be non-coincidently mated with the patient tissue at the same time/duration or at different times/durations.

Other options for secondary items 104 include a cutting indicator 214, such as that shown with the secondary item 104″ of FIG. 2D, and a drill guide 216, such as that shown with the secondary item 104‴ of FIG. 2E. A cutting indicator 214, when present, is configured for a guiding relationship with a cutting implement performing at least one of a resection and a trimming of the patient tissue. A "guiding relationship" is used herein to indicate that the "guiding" component steadies and/or directs the motion of the "guided" component. For reasons which will later become apparent, a rim 218 of the secondary item 104‴ of FIG. 2E may also serve as a cutting indicator 214. A drill guide 216, when present, guides a penetrating implement into the patient tissue.

Each mounting feature 108 of the primary locating block 102 may be configured for engagement with at least one secondary item 104 in the predetermined secondary mounting relationship. For example, the secondary item 104 could include a secondary mounting feature 220 for engagement with the mounting feature 108 of the primary locating block 102 in the predetermined secondary mounting relationship. The secondary mounting relationship may be custom-configured for the patient tissue responsive to preoperative imaging of the patient tissue, and may be made patient-specific by a configuration of the mounting feature 108 and/or the secondary item 104. It is contemplated that, for most applications of the present invention, there will only be one reasonable secondary mounting relationship for each secondary item 104 with the primary locating block 102, to provide the user with a high degree of confidence that the preoperatively planned reference indications are being transferred reliably to the actual patient tissue. Keys and/or slots, located on one or both of the primary locating block 102 and the secondary item 104, may be used to help guide and/or secure the secondary item in a predetermined relationship with the primary locating block.

Optionally, at least one anchoring feature could be provided to one or both of the primary locating block 102 and the secondary item(s) 104 for providing at least one of securement, stability, and position indication for that portion of the apparatus 100 relative to the patient tissue. For example, and as shown in FIGS. 2A and 2B, the anchoring feature includes a plurality of anchoring structures 222 which are each configured to guide an anchoring pin (not shown) into the patient tissue at a predetermined location and trajectory.

(The location and/or trajectory could be preoperatively chosen, for example, to anchor into solid patient tissue or to avoid disturbing pathologic patient tissue.) In the FIGS. 2A and 2B arrangement, the anchoring pin(s) are operative to provide at least one of securement, stability, and position indication for the primary locating block 102 relative to the patient tissue in the primary mating orientation, as will be discussed below. Similarly, as shown in FIG. 2E, the secondary item 104‴ can include one or more anchoring structures 222 which may be used in cooperation with an anchoring pin (not shown) to provide at least one of securement, stability, and position indication for the secondary item relative to the patient tissue at a predetermined location, whether or not the anchoring structure(s) of the secondary item provide trajectory guidance.

Using the positioning indicator 210, cutting indicator 214, drill guide 216, and/or any other suitable structure, the secondary item 104—whatever its specific configuration—may facilitate at least one of resection, repositioning, drilling, trimming, and configuration (e.g., positioning) verification of the patient tissue. These and similar properties are referenced collectively herein as providing "reference indication" to the patient tissue. Reference indication may be useful, for example, in physically transferring preoperatively planned virtual dimensions, angles, resection locations, and other physical properties to the actual patient tissue. To aid this effort, a predetermined secondary mounting relationship may be provided to the apparatus 100.

As shown in FIGS. 2A and 2B, the primary locating block 102 may include one or more mounting features 108, with the depicted example embodiment including a keyed female-type mounting feature 108′ and a keyed male-type mounting feature 108″, both of which are configured to removably accept a correspondingly shaped secondary mounting feature 220 in a male-to-female (or female-to-male) mounting relationship. By way of example, the secondary item 104′ of FIG. 2C is depicted as including a male-type secondary mounting feature 220 configured for mating with the keyed female-type mounting feature 108′, and the secondary items 104″ and 104‴ of FIGS. 2D and 2E both are depicted as including a ring-type female-type secondary mounting feature (including a cylindrical feature extending circumferentially around all or part of the mounting feature 108″) for mating with the keyed male-type mounting feature 108″, though any suitably-structured mounting features 108 may be provided by one of ordinary skill in the art. The "keyed" features, when present, may include cavities 224 and/or protrusions 226 on either or both of the primary locating block 102 and the secondary item 104, or any other structures which may help to positively locate, and optionally help maintain, the structures of the apparatus 100 in the predetermined secondary mounting relationship. Optionally, a securement aperture 228 could be provided in either or both of the primary locating block 102 and the secondary item 104 to accept a pin, bolt, screw, nail, wire, or other fastener to help maintain the structures of the apparatus 100 in the predetermined secondary mounting relationship.

Because at least the primary mating surface 106 portion of the primary locating block 102 is contemplated to be custom-manufactured for each patient, it also may be possible to custom-configure the mounting feature(s) 108 of the primary locating block, as well, to accept a secondary item 104 in a particular patient-specific orientation. For example, the keyed female-type mounting feature 108′ and/or the keyed male-type mounting feature 108″ could have appropriate configurations, optionally including cavities 224 and/or protrusions 226 having predetermined relationships with the primary mating surface 106 so that any secondary item 104 mated to the mounting feature will extend therefrom at a predetermined angle. Stated differently, though the keyed male-type mounting feature 108″ has a cavity 224 at a particular angular relationship with respect thereto, that cavity 224 could be rotated around the circumference of the mounting feature 108" so that the cavity 224 is located in another angular relationship with respect to the mounting feature (e.g., further clockwise or counterclockwise, in the orientation of FIG. 2B), which will result in a mated secondary item 104 achieving a desired and potentially patient-specific orientation with the primary mating surface 106 and, by extension, with the patient tissue.

One of ordinary skill in the art will understand that the secondary mounting relationship, in which a secondary item 104 is held (usually removably held) by the primary locating block 102 in a predetermined relative position, may be made patient-specific by the arrangement and configuration of the mounting feature 108 which interacts with the secondary item. The secondary mounting relationship also or instead can be made patient-specific by the arrangement and configuration of the secondary mounting feature 220 (of the secondary item 104) which interacts with the primary locating block 102 (e.g., the arrangement and configuration of the cavities 224, protrusions 226, or any other portion of the secondary mounting feature 220 or any mounting feature 108 of the primary locating block). In this manner, one of ordinary skill in the art will be able to design a patient-specific component of the apparatus 100 (e.g., the primary locating block 102) which interacts with one or more stock or non-patient-specific components of the apparatus (e.g., the secondary item(s) 104) to provide some degree of patient-specificity in the apparatus as a whole. This patient-specificity of an apparatus 100 for providing a reference indication may be desirable for facilitating a surgical operation and might otherwise be unavailable, prohibitively expensive, and/or undesirably time-consuming to achieve.

Figure 3:
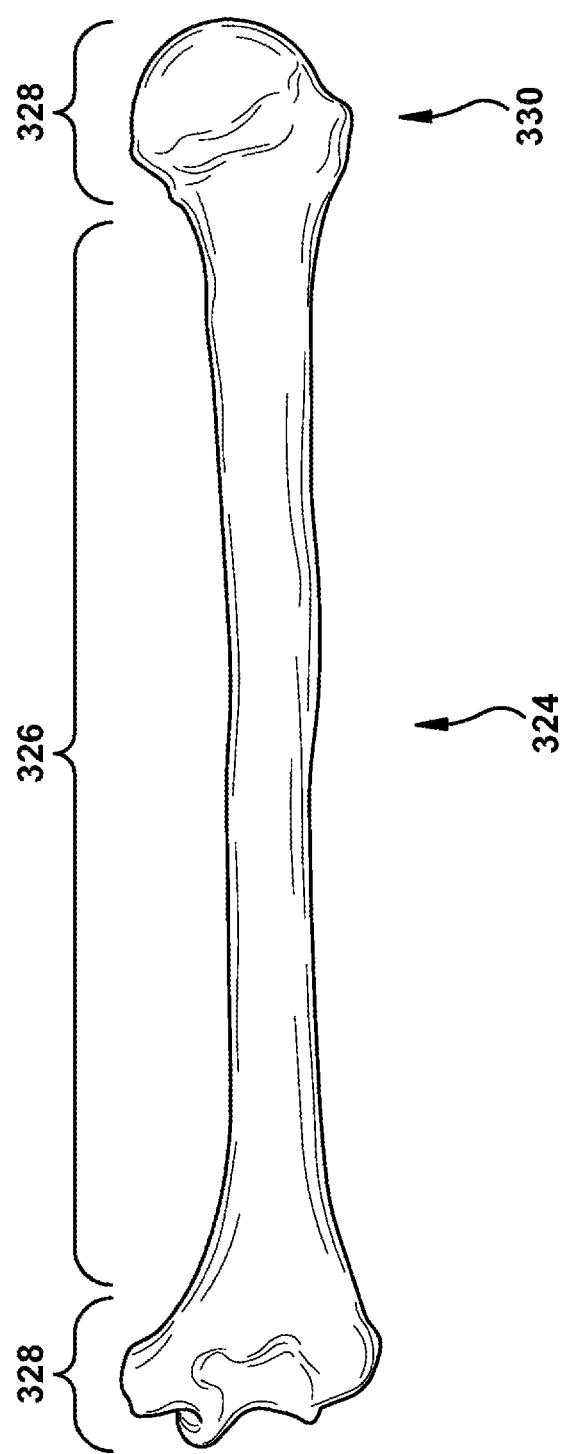
FIG. 3 is a side view of an example use environment for the embodiment of FIG. 1.

An example patient tissue use environment for an apparatus 100 according to an embodiment of the present invention is shown in FIG. 3. The patient tissue depicted in FIG. 3 is a long bone, more specifically a humerus 324, though the apparatus 100 may be used with any suitable patient tissue. The central portion of the humerus 324 is a diaphysis (shown approximately at 326), with an epiphysis (shown approximately at 328) at either end of the humerus. The below description presumes that the humeral head 330 (the epiphysis 328 on the right side of the page, in the orientation of FIG. 3) is being resected and the intramedullary canal (i.e., the interior of the diaphysis 326) is being broached, reamed, and/or drilled out to accept a stem of a humeral prosthetic shoulder joint component, with at least a portion of the surgical procedure being performed with the assistance of the apparatus 100. The apparatus 100, shown in various optional configurations in FIGS. 1 and 4-9, may be at least partially custom-manufactured for a particular patient responsive to preoperative imaging of the patient tissue. For example, the apparatus 100, or portions thereof, may be wholly custom-made (e.g., using rapid prototyping techniques) or may be modified from a stock guide or guide blank (not shown). It is contemplated that at least a part of the apparatus 100 is a patient-specific, single-use, bespoke feature suited only for use at the indicated surgical site, though one of ordinary skill in the art could create an apparatus—or components thereof—which uses a patient-specific "disposable" structure connected to a stock, generic "reusable" carrier (e.g., a reusable secondary item 104' could carry a disposable/replaceable positioning indicator 210). However, for cost and complexity reasons, users of the apparatus 100 in particular applications of the present invention may prefer to have a patient-specific and disposable primary locating block 102 and an assortment of both reusable and patient-specific/disposable secondary items 104, and this is the situation that will be presumed in the below description.

Regardless of the whole/partial custom manufacture status, the apparatus 100 may be configured responsive to at least one of preoperative imaging of the patient tissue and preoperative selection of the stock prosthetic implant. For example, a system similar to that of co-pending U.S. Provisional Patent Application No. 61/408,392, filed Oct. 29, 2010 and titled "System of Preoperative Planning and Provision of Patient-Specific Surgical Aids" (the entire contents of which are incorporated herein by reference), or any suitable preoperative planning system, could be used. In this manner, a user can create a patient tissue model for observation, manipulation, rehearsal, or any other preoperative tasks.

The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface.

During preoperative planning, the user can view the patient tissue model and, based upon knowledge of other patient characteristics (such as, but not limited to, height, weight, age, and activity level), choose a desired stock prosthetic implant. Because three-dimensional image models are available of many stock prosthetic implants, the user may be able to "install" the stock prosthetic implant virtually in the patient tissue model via a preoperative computer simulation. During such a simulation, the user can adjust the position of the stock prosthetic implant with respect to the patient tissue, even to the extent of simulating the dynamic interaction between the two, to refine the selection, placement, and orientation of the stock prosthetic implant for a desired patient outcome.

Once a chosen stock prosthetic implant has been virtually placed in a desired position and orientation with respect to the patient tissue, it will be understood that some mechanical modification—including, but not limited to, resection, repositioning, drilling, trimming—might need to be made to the native patient tissue to accomplish the desired prosthetic implant placement. The modification information for the particular patient tissue achieved via preoperative imaging and/or computer simulation/modeling may be transferred to a physical aid for the user through the custom manufacture of an apparatus 100. When the preoperative planning has been finalized, a virtual apparatus 100 may be generated, having particular characteristics chosen with respect to the virtual implant and the virtual patient tissue. The user may then have the opportunity to adjust the virtual implant, if desired, before a physical implant is produced.

The patient's name, identification number, surgeon's name, and/or any other desired identifier may be molded into, printed on, attached to, or otherwise associated with the apparatus 100, or portions thereof, in a legible manner. The apparatus 100 may be made of any suitable material or combination of materials, and may be created using any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

Figure 4:
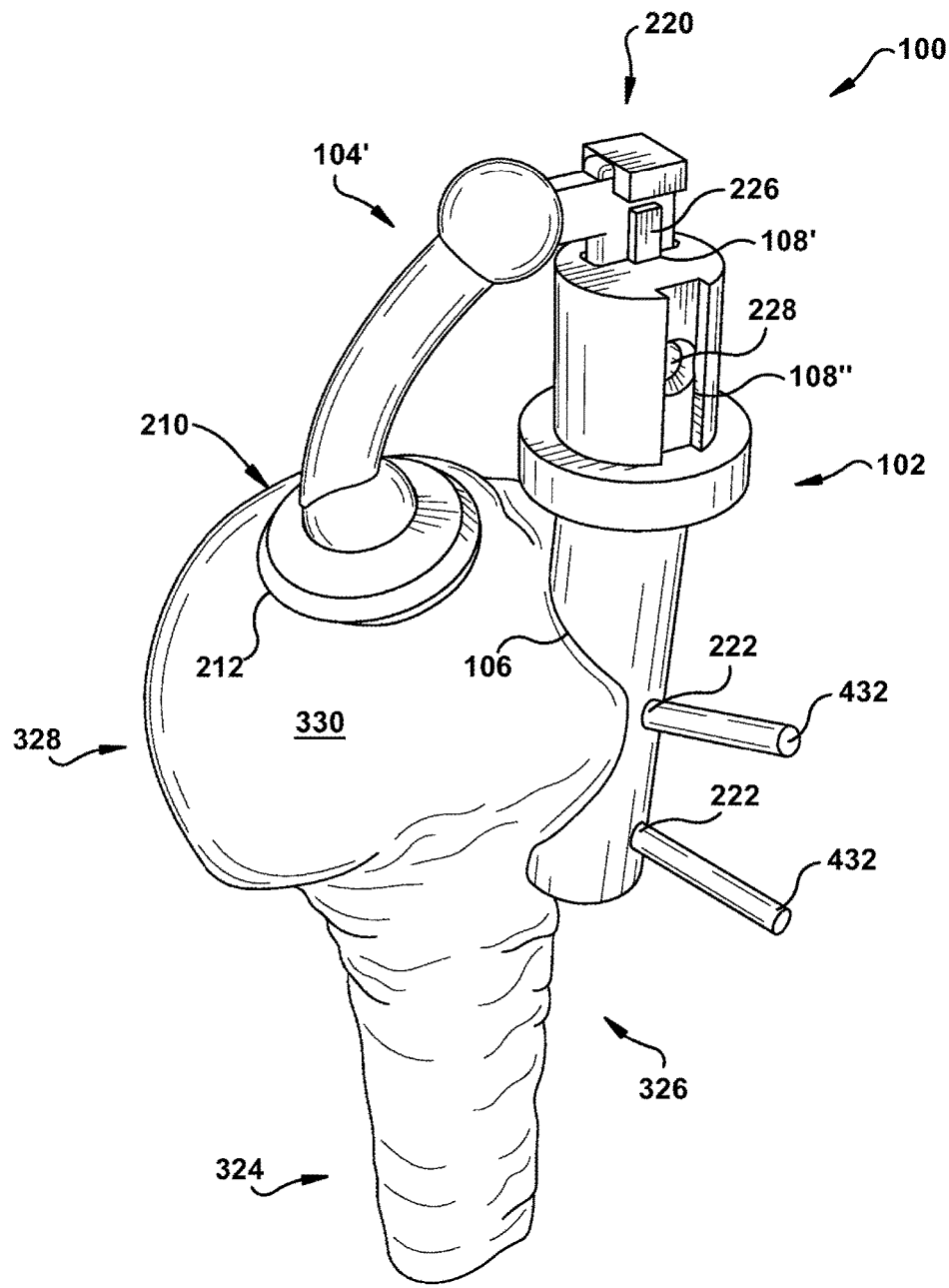

Regardless of how the components thereof were provided, FIG. 4 depicts a patient-specific secondary item 104' which has been brought into selective engagement with the primary locating block 102 in a predetermined secondary mounting relationship to form an apparatus 100, which has been positioned in contact with the humerus 324. The primary mating surface 106 of the primary locating block 102 has been placed into a predetermined primary mating orientation with a nontarget portion of the humerus 324—i.e., a portion of the humerus which is relatively constant and unchanging during the use of the apparatus 100, and the secondary mating surface 212 of the secondary item 104' has been placed into a predetermined secondary mating orientation with a target portion of the humerus. In the example of FIGS. 4-9, the nontarget portion of the humerus 324 includes at least a portion of the diaphysis of the humerus, and a target portion of the humerus includes at least a portion of the epiphysis 328 of the humerus.

As shown in FIG. 4, the secondary item 104' is of the type which includes a positioning indicator 210, and a secondary mating surface 212 of the positioning indicator mates with a predetermined portion of the humeral head 330 to help confirm the position of the apparatus 100 with respect to the humerus 324, and optionally to help steady the primary locating block 102 during the initial stages of use of the apparatus in the surgical procedure. (Both of these functions of the secondary item 104' may be considered the provision of a reference indication.) Here, the primary mating surface 106 of the primary locating block 102 has been mated with at least a portion of the bicipital groove (not shown). Once the user is reasonably confident that the primary locating block 102 is in the desired primary mating orientation with respect to the humerus 324, one or more anchoring pins 432 may interact with respective anchoring structures 222 to substantially secure the primary locating block 102 to the humerus in the aforementioned manner.

Figure 5:
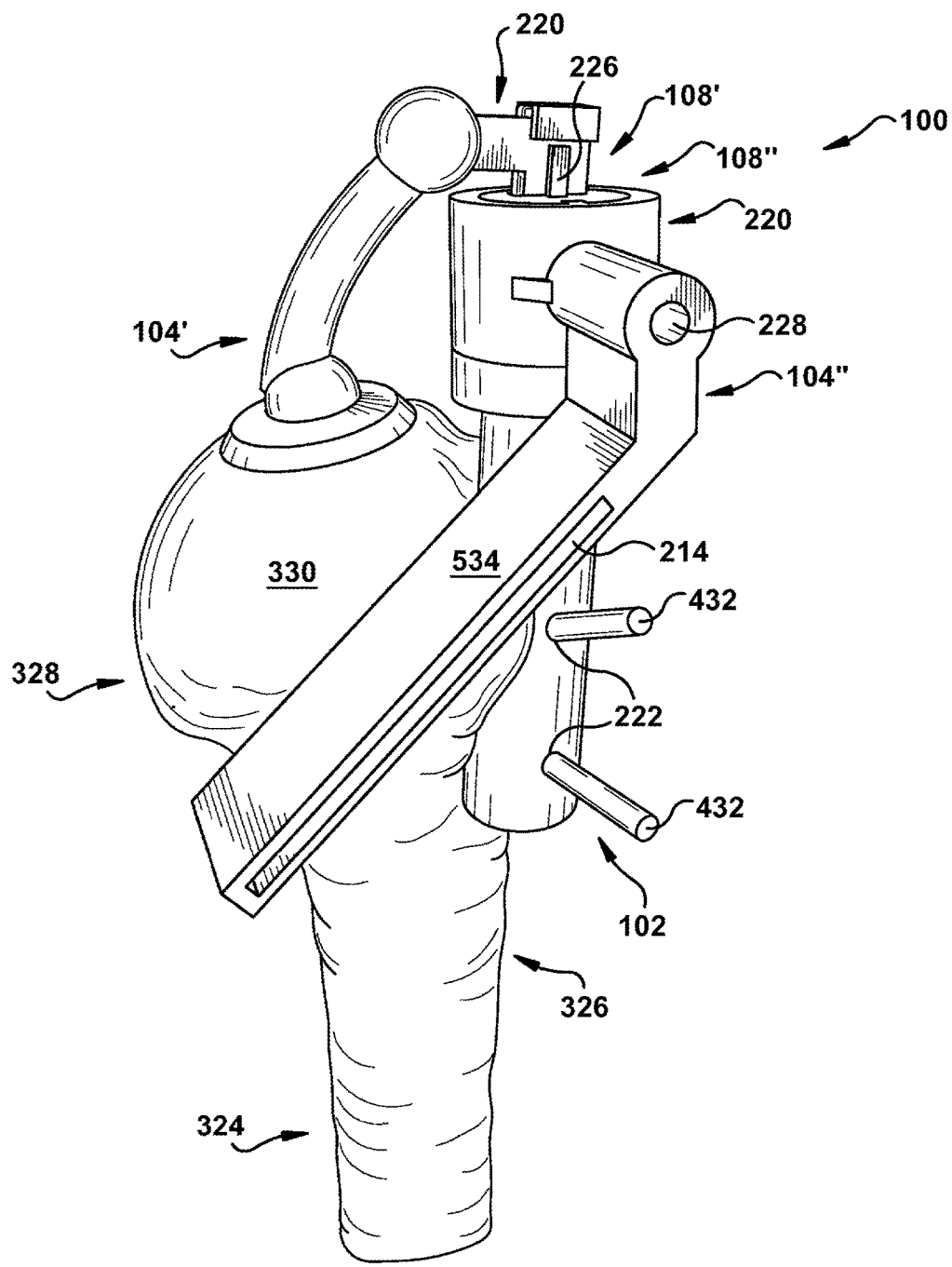

Turning to FIG. 5, the patient-specific secondary item 104' has been left in the secondary mounting relationship with the keyed female-type mounting feature 108' (optionally to steady the apparatus 100 during this phase of surgery), and a stock (non-patient-specific) secondary item 104" has been placed into a secondary mounting relationship with the keyed male-type mounting feature 108" of the primary locating block 102. A cutting indicator 214 (here, a slot in the secondary item 104") has been placed at a desired cutting plane location for resection of the humeral head 330. Although the secondary item 104" is a stock component, one of ordinary skill in the art can readily understand, with reference to FIG. 5, how arrangement and orientation of the keyed male-type mounting feature 108" of a patient-specific primary locating block 102—e.g., setting a desired rotation position of the cavity 224 with respect to the rest of the mounting feature 108"—will dictate a desired patient-specific secondary mounting relationship sufficient to place even a stock secondary item 104" in a desired relative position to the humeral head 330. For example, the secondary mounting relationship could be adjusted during preoperative planning to configure a patient-specific primary locating block 102 and thereby place the cutting indicator 214 at a desired angle with respect to the humeral head 330.

As shown, the secondary item 104" includes a cutting indicator 214 which is a slot configured to accept and guide a surgical saw to resect the humeral head 330 as desired. The secondary item 104" also or instead could guide a surgical saw or other cutting instrument along a top guiding surface 534 thereof to perform the desired resection. Because the surgical saw or other cutting instrument is sharp and may move unpredictably due to irregularities in the patient tissue, or due to imprecise use of the tool, it may be desirable for the secondary item 104" containing the cutting indicator 214 to be at least partially made of metal or other material(s) that are durable and generally resistant to being fragmented. The material choice should be selected to avoid shedding of debris from the secondary item 104" into the patient's tissue due to contact between the tool and the secondary item. A metal (or other durable-material) patient-specific construct may be difficult and/or expensive to fabricate, however. The present invention provides for the use of a stock, non-patient-specific secondary item 104" to be reused for multiple patients because the configuration of the primary locating block 102 and the specifics of the secondary mounting relationship allow patient-customization of the guiding function of the cutting indicator 214 without requiring patient-customization of the secondary item 104" containing that cutting indicator.

Figure 6:
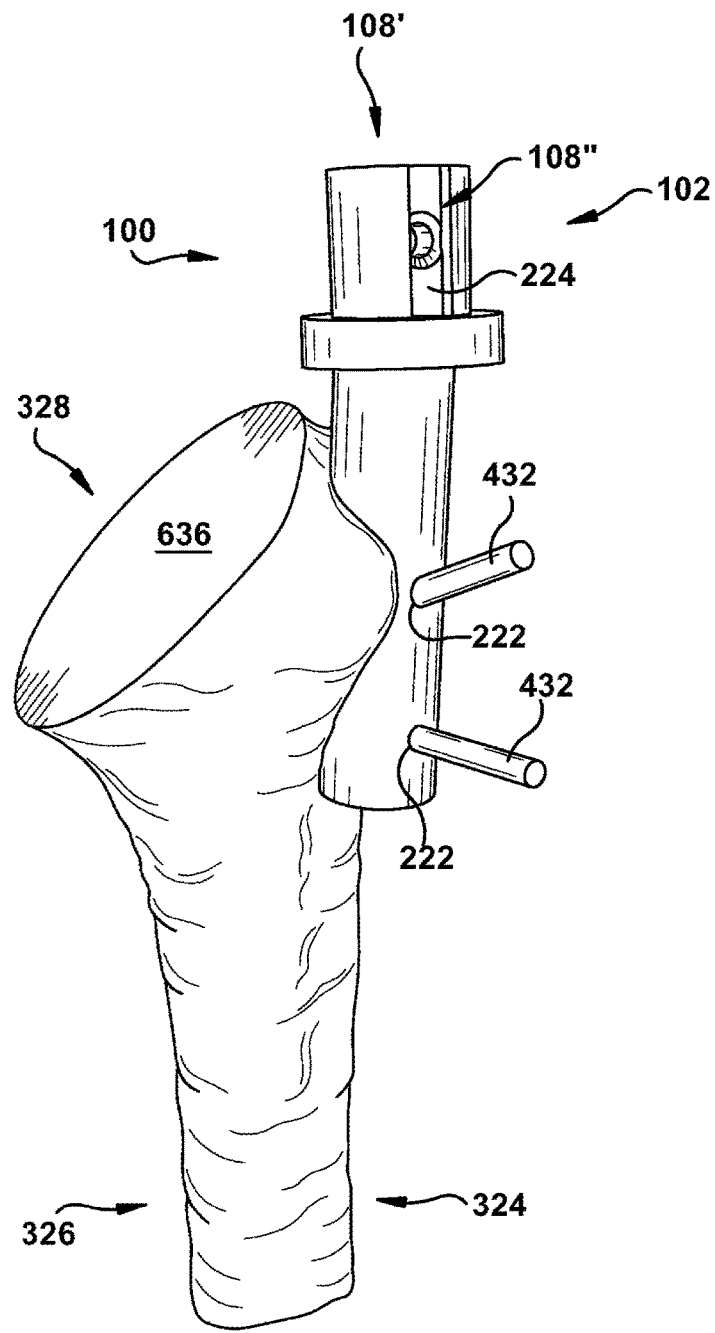

In FIG. 6, the humeral head 324 has been removed along a prescribed cutting plane to leave an osteotomy surface 636. The secondary items 104' and 104" have been removed from the mounting features 108' and 108", respectively, leaving the primary locating block 102 anchored to the nontarget tissue of the humerus 324 by the anchoring pins 432 interacting with the anchoring structures 222.

Figure 7:
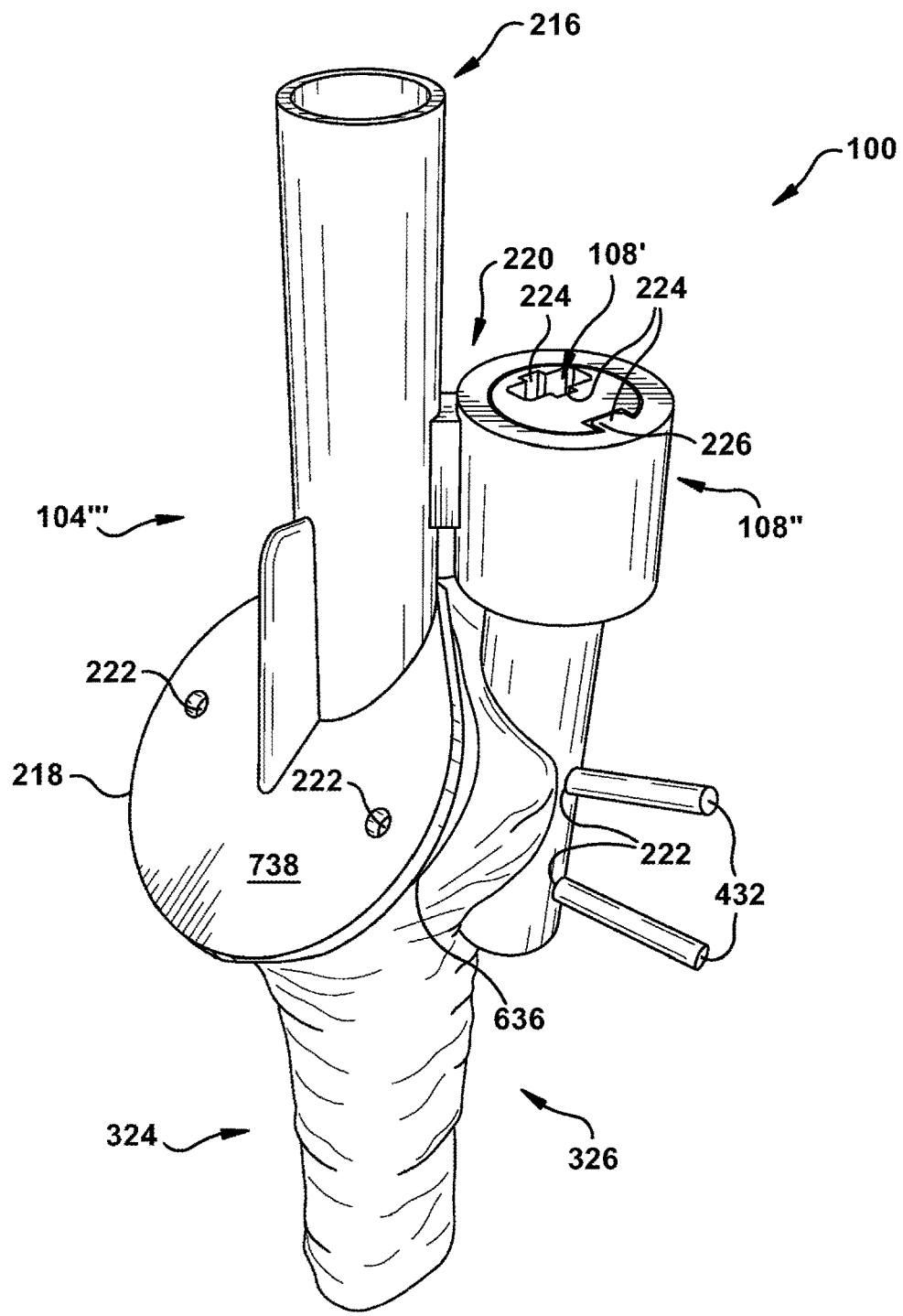

Continuing to FIG. 7, a patient-specific secondary item 104'" has been placed into a secondary mounting relationship with the mounting feature 108" of the primary locating block 102, while mounting feature 108' has been left empty. Secondary item 104'" includes an osteotomy plate 738 which extends at a predetermined angle from the locating block 102 when the secondary item 104'" is in the secondary mounting relationship. It is contemplated that this angle will bring the osteotomy plate 738 into substantially full contact with the osteotomy surface 636 of the humerus 324 and therefore serve as a positioning indicator by providing a reference indication that either verifies that the humeral head 330 was resected according to the preoperative plan or guides additional machining operations to correct a resection that did not occur as planned.

Figure 8:
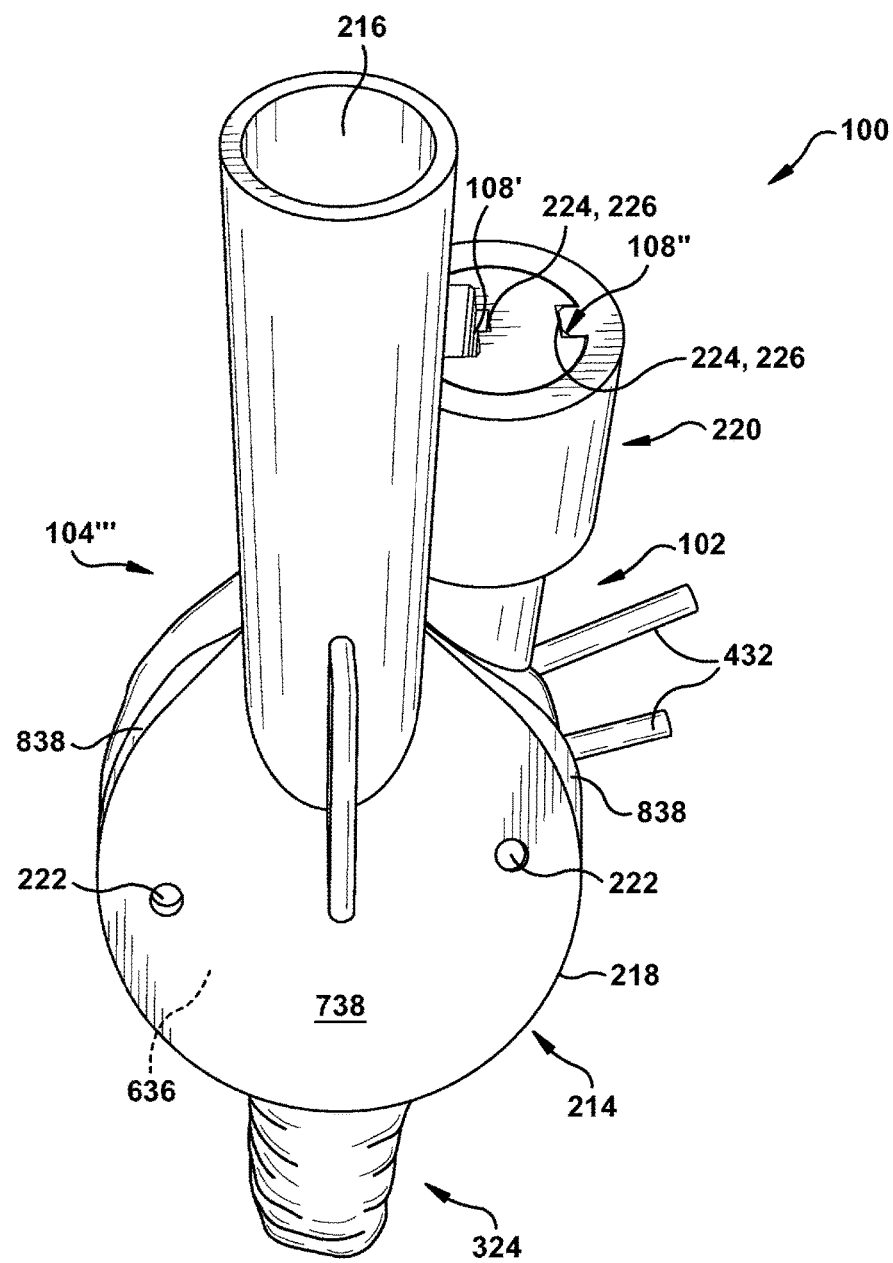

FIGS. 8 and 9 depict various additional views of the arrangement of FIG. 7, though the apparatus 100 remains substantially unchanged from the view of FIG. 7 to the view of FIG. 8. In FIG. 8, a top view of the osteotomy surface 636 and overlying osteotomy plate 738 is shown. Optionally, and as depicted here, the osteotomy plate 738 may bear a relationship to the prosthetic shoulder joint component being installed such that the osteotomy plate represents a "footprint" of the prosthetic shoulder joint component. Additionally or alternately, the osteotomy plate 636 can have a perimeter/profile shape chosen by the user (not necessarily based upon a prosthetic component) to act as a template or guide to help impart/transfer any desired shape or borders to the humerus 324 or another remaining patient tissue structure. Whether or not this implant "footprint" relationship is present, portions of the osteotomy surface 636 visible from above and located lateral to the rim 218 of the secondary item 104'" may be undesirable osteophytes 838 and may be removed by the user to smooth the eventual interface between the humerus 324 and the prosthetic shoulder joint component. In this way, the rim 218 acts as a template or cutting indicator 216 to guide the user in resecting or otherwise removing undesirable patient tissue during the surgical procedure.

In FIG. 9, the osteophytes 838 have been removed, and the orientation of this Figure instead emphasizes the drill guide 216 of the secondary item 104'''. The secondary item 104''' includes a drill guide 216 for providing a reference indication to guide drilling, broaching, rasping, or other machining of the diaphysis 326 to accommodate a penetrating portion of the prosthetic shoulder joint component. One or more removable drill guide spacers 940 could be associated, as a group or singly, with the drill guide 216. (As shown here, the drill guide spacer(s) 940 are nested within the drill guide 216 and may serve as "bushings" to shield contact between the drill guide and the drill or other tool being guided.) Through sequential use of the drill guide spacer(s) 940, a succession of drilling, broaching, rasping, or other machining operations can be guided to gradually enlarge an aperture in the patient tissue through use of successively larger tools. The drill guide 216 may be patient-specific to guide a drill 1042 or other penetrating implement (shown schematically in FIG. 10) to carry out a preoperatively planned drilling or other penetrating procedure at a predetermined location having a desired relationship to the body of the humerus 324. Optionally, the drill guide 216 may also include a drill stop (e.g., an upper rim of the drill guide structure) which provides a reference indication or even restricts excessive penetration of the penetrating implement into the intramedullary canal of the diaphysis 326.

When the desired reference indications have all been performed, the apparatus 100 may be removed from the patient tissue and the surgical procedure can then proceed apace. The patient-specific portions of the apparatus 100 are discarded and the stock or non-patient-specific portions of the apparatus 100 are sterilized and returned to inventory for later use with other patients.

The secondary mounting relationship shown in the Figures includes a male-to-female frictional fitting interaction between the mounting feature(s) 108 of the primary locating block 102 and the secondary mounting feature(s) 220 of the secondary item(s) 104. It is contemplated that the frictional fit between these two components be firm enough to retain the secondary item(s) 104 in engagement with the primary locating block 102 until the user exerts a reasonable force to remove the secondary item(s) from the primary locating block. Generally, the user will wish to perform this removal without dislodging the primary mounting surface 106 from the patient tissue. However, one of ordinary skill in the art can readily provide mounting feature(s) 108 of the primary locating block 102 and secondary mounting feature(s) 220 of the secondary item(s) 104 which interact and engage together in any desired manner, and using any desired intermediary fastening means/techniques, such as, but not limited to, adhesives, frictional engagement of any type (e.g., male/female roles reversed from those shown), additional fasteners (e.g., cotter pins), threadable engagement, captured-ball mechanisms, external-collar mechanisms, magnets, securement aperture(s) 228, any other suitable mounting feature types, or any combination thereof.

Additionally, one of ordinary skill in the art could also provide symmetrical or otherwise non-directional/non-patient-specific mounting feature(s) 108 of the primary locating block 102 and/or secondary mounting feature(s) 220 of the secondary item(s) 104 which can fit together in many different secondary mounting relationships. In order to make such an arrangement patient-specific, the mounting feature(s) 108 of the primary locating block 102 and/or secondary mounting feature(s) 220 of the secondary item(s) 104 could include visual indicators (e.g., a radial/degree scale on one or both of the mating mounting features 108 and 220) to assist the user with achieving a desired predetermined relative position between the primary locating block and the secondary item when in the secondary mounting relationship.

Figure 11:
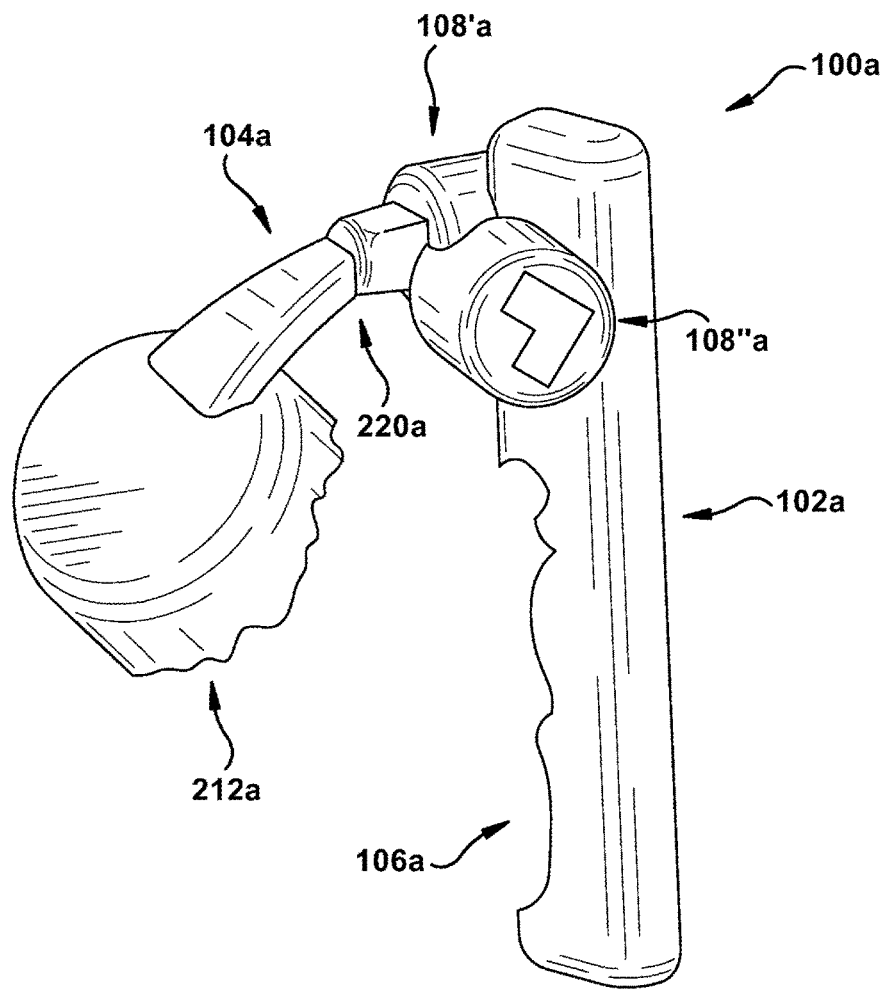
FIG. 11 is a perspective side view of a configuration of an embodiment of the present invention.

FIG. 11 depicts an apparatus 100 according to a second embodiment of the present invention. The apparatus 100 of FIG. 11 is similar to the apparatus 100 of FIGS. 1-9 and therefore, structures of FIG. 11 that are the same as or similar to those described with reference to FIGS. 1-9 have the same reference numbers with the addition of a lower-case "a". Description of common elements and operation similar to those in the previously described embodiment will not be repeated with respect to the second embodiment.

As shown in FIG. 11, the primary locating block 102a may include one or more mounting features 108a, with the depicted example embodiment including a quarter-round mounting feature 108'a and an ell-shaped mounting feature 108"a, both of which are configured to removably accept a correspondingly shaped secondary mounting feature 220a in a male-to-female mounting relationship. The secondary items 104a of FIG. 11 includes a quarter-round secondary mounting feature 220a for mating with the quarter-round mounting feature 108'a, and another secondary item (not shown) for use with the second embodiment of FIG. 11 might include an ell-shaped secondary mounting feature for mating with the ell-shaped mounting feature 108"a. Because at least the primary mating surface 106a portion of the primary locating block 102a is contemplated to be custom-manufactured for each patient, it also may be possible to custom-configure the mounting feature(s) 108a of the primary locating block, as well, to accept a secondary item 104a in a particular patient-specific orientation. For example, the quarter-round mounting feature 108'a and/or the ell-shaped mounting feature 108"a could be placed into a particular angular relationship with the primary mating surface 106a so that any secondary item 104a mated to the mounting feature will extend therefrom at a predetermined angle. Stated differently, though the ell-shaped mounting feature 108"a has a vertex pointing toward the right in the orientation of FIG. 11, that ell shape could be rotated so that the vertex points in any other desired direction (e.g., up, down, to the left, etc.) which will result in a mated secondary item 104a achieving a desired orientation with the primary mating surface 106a and, by extension, with the patient tissue.

One of ordinary skill in the art can readily understand, with reference to FIG. 11, how arrangement and orientation of the quarter-round mounting feature 108'a and/or the ell-shaped mounting feature 108"a—e.g., setting a desired rotation position of the quarter-round or ell-shape with respect to the rest of the primary locating block 102a—will dictate a desired patient-specific secondary mounting relationship sufficient to place the secondary item 104a in a desired relative position to the humeral head 330a. For example, the secondary mounting relationship could be adjusted during preoperative planning to place a cutting indicator (not shown) at a desired angle with respect to the humeral head.

While aspects of the present invention have been particularly shown and described with reference to the preferred embodiment above, it will be understood by those of ordinary skill in the art that various additional embodiments may be contemplated without departing from the spirit and scope of the present invention. For example, any of the described structures and components could be integrally formed as a single piece or made up of separate sub-components, with either of these formations involving any suitable stock or bespoke components and/or any suitable material or combinations of materials. It is contemplated that at least one of the primary locating block 102 and secondary item(s) 104 may be reusable (optionally sterilizable), and at least one of the primary locating block and secondary item(s) may be disposable. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A variety of schemes are described herein for placing the apparatus 100 into the predetermined position with respect to the patient tissue, and these schemes can be used singly or in any suitable combination for a particular application of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. The apparatus 100, or portions thereof, could be anchored to the patient tissue in any suitable manner, such as, but not limited to, adhesives, integral pegs, other fasteners, frictional engagement, magnets, securement aperture(s) 228, any other suitable mounting feature types, or any combination thereof. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

The invention claimed is:

1. An apparatus for providing a reference indication to a patient humerus, the apparatus comprising:
   a primary locating block including a patient-specific primary mating surface contoured and configured for mating contact with at least a portion of a diaphysis of the humerus, the primary mating surface being custom-configured to mate with the humerus in a predetermined primary mating orientation responsive to preoperative imaging of the patient humerus, and at least one mounting feature; and
   at least one secondary item configured for selective engagement with the primary locating block and including a patient-specific secondary mating surface being contoured and configured for mating contact with at least a portion of the epiphysis of the humerus, the secondary item being custom-configured to mate with the humerus in a predetermined secondary mating orientation responsive to preoperative imaging of the humerus, the secondary mating orientation being non-coincident with the primary mating orientation, and the secondary item providing a first reference indication to the portion of the epiphysis of the humerus;
   wherein the mounting feature of the primary locating block is configured for engagement with the at least one secondary item in a predetermined secondary mounting relationship, the secondary mounting relationship being custom-configured for the patient humerus responsive to preoperative imaging of the patient humerus such that the primary locating block and the at least one secondary item are in the predetermined secondary mounting relationship when respectively and concurrently in said mating contact with at least the diaphysis and the epiphysis of the patient humerus.

2. The apparatus of claim 1, further comprising at least another secondary item configured for selective engagement with the primary locating block, the other secondary item being a noncustomized stock secondary item providing a second reference indication to the epiphysis distinct from the first reference indication, the mounting feature of the primary locating block being configured for engagement with the other secondary item in another predetermined secondary mounting relationship.

3. The apparatus of claim 2, wherein the mounting relationship between the other secondary item and the primary locating item is made patient-specific by a configuration of the other secondary item.

4. The apparatus of claim 2, wherein at least one of the secondary items includes a cutting indicator for a guiding relationship with a cutting implement performing at least one of a resection and a trimming of the patient humerus.

5. The apparatus of claim 2, wherein at least one of the secondary items includes a drill guide for guiding a penetrating implement into the patient humerus.

6. The apparatus of claim 1, wherein the secondary item includes a positioning indicator for verifying the position of at least a portion of the apparatus with respect to the patient humerus.

7. The apparatus of claim 1, wherein the primary locating block includes at least one anchoring feature for providing at least one of securement, stability, and position indication for the primary locating block relative to the patient humerus in the primary mating orientation.

8. The apparatus of claim 7, wherein the anchoring feature includes an anchoring structure configured to guide an anchoring pin into the patient tissue at a predetermined location and trajectory, the anchoring pin being operative to provide at least one of securement, stability, and position indication for the primary locating block relative to the patient humerus in the primary mating orientation.

9. The apparatus of claim 2, wherein at least one of the secondary items includes a secondary mounting feature for engagement with the mounting feature of the primary locating block in the predetermined secondary mounting relationship.

10. The apparatus of claim 2, wherein the secondary items facilitate at least one of resection, repositioning, drilling, trimming, and configuration verification of the patient tissue.

11. A method of providing a reference indication to a patient humerus, the method comprising:
   obtaining a primary locating block including a patient-specific primary mating surface contoured and configured for mating contact with at least a portion of a diaphysis of the humerus, and at least one mounting feature;

mating the primary mating surface with the patient humerus in a primary mating orientation predetermined at least partially responsive to preoperative imaging of the patient tissue;

obtaining at least one secondary item including a patient-specific secondary mating surface being contoured and configured for mating contact with at least a portion of the epiphysis of the humerus;

engaging the mounting feature of the primary locating block with the at least one secondary item in a predetermined secondary mounting relationship, the secondary mounting relationship being custom-configured for the patient humerus responsive to preoperative imaging of the patient humerus; and mating the secondary mating surface with the patient humerus in a secondary mating orientation predetermined at least partially responsive to preoperative imaging of the patient humerus, the secondary mating orientation being non-coincident with the first mating orientation;

obtaining a first reference indication to at least a portion of the patient humerus with the secondary item when the primary mating surface and the secondary mating surface are respectively and concurrently in said mating with at least the diaphysis and the epiphysis of the patient humerus.

12. The method of claim 11, further comprising:

obtaining at least another secondary item configured for selective engagement with the primary locating block, the other secondary item being a noncustomized stock secondary item providing a second reference indication to the epiphysis distinct from the first reference indication, engaging the mounting feature of the primary locating block with the other secondary item in another predetermined secondary mounting relationship, and obtaining the second reference indication to the portion of the epiphysis of the patient humerus with the other secondary item copied to the primary locating block and with the primary mating surface in said mating with at least the diaphysis of the patient humerus.

13. The method of claim 12, including engaging the mounting feature of the primary locating block with the other secondary item is patient-specific by a configuration of the other secondary item.

14. The method of claim 12, wherein at least one of the secondary items includes comprises obtaining a cutting indicator, and the method includes the step of placing the cutting indicator into a guiding relationship with a cutting implement performing at least one of a resection and a trimming of the patient humerus.

15. The method of claim 12, wherein at least one of the secondary items includes a drill guide, and the method includes the step of guiding a penetrating implement into the patient tissue with the drill guide.

16. The method of claim 11, wherein the secondary item includes a positioning indicator, and the method includes the step of verifying the position of at least a portion of the apparatus with respect to the patient humerus with the positioning indicator.

17. The method of claim 11, including the step of obtaining at least one of securement, stability, and position indication for the primary locating block relative to the patient humerus in the primary mating orientation using an anchoring feature.

18. The method of claim 17, wherein the anchoring feature includes an anchoring aperture, and the method includes the steps of:

using the anchoring structure to guide an anchoring pin into the patient tissue at a predetermined location and trajectory; and obtaining at least one of securement, stability, and position indication for the primary locating block relative to the patient humerus in the primary mating orientation with the anchoring pin.

19. The method of claim 12, wherein at least one of the secondary items includes a secondary mounting feature, and the method includes the step of engaging the secondary mounting feature with the mounting feature of the primary locating block in the predetermined secondary mounting relationship.

20. The method of claim 12, wherein at least one of the secondary items facilitates at least one of resection, repositioning, drilling, trimming, and configuration verification of the patient tissue.

* * * * *